United States Patent
Wang et al.

(10) Patent No.: US 12,056,424 B2
(45) Date of Patent: Aug. 6, 2024

(54) SIMULATION OF MICROSTRUCTURE EVOLUTION OF MATERIAL AS SOLVED BASED ON EXPONENTIAL TIME-DIFFERENCE FORMAT

(71) Applicants: CHINA INSTITUTE OF ATOMIC ENERGY, Beijing (CN); COMPUTER NETWORK INFORMATION CENTER, CHINESE ACADEMY OF SCIENCES, Beijing (CN)

(72) Inventors: Yangang Wang, Beijing (CN); Xinfu He, Beijing (CN); Jian Zhang, Beijing (CN); Zhikuang Xin, Beijing (CN); Yankun Dou, Beijing (CN); Ningming Nie, Beijing (CN); Lixia Jia, Beijing (CN); Jue Wang, Beijing (CN); Wen Yang, Beijing (CN)

(73) Assignees: CHINA INSTITUTE OF ATOMIC ENERGY, Beijing (CN); COMPUTER NETWORK INFORMATION CENTER, CHINESE ACADEMY OF SCIENCES, Beijing (CN)

( * ) Notice: Subject to any disclaimer, the term of this patent is extended or adjusted under 35 U.S.C. 154(b) by 362 days.

(21) Appl. No.: 17/283,426

(22) PCT Filed: Oct. 9, 2020

(86) PCT No.: PCT/CN2020/120032
§ 371 (c)(1),
(2) Date: Apr. 7, 2021

(87) PCT Pub. No.: WO2021/068901
PCT Pub. Date: Apr. 15, 2021

(65) Prior Publication Data
US 2022/0058311 A1   Feb. 24, 2022

(30) Foreign Application Priority Data

Oct. 9, 2019  (CN) .......................... 201910953927.X
Oct. 9, 2019  (CN) .......................... 201910957443.2

(51) Int. Cl.
G06F 30/20 (2020.01)
G06F 17/14 (2006.01)
(Continued)

(52) U.S. Cl.
CPC ............ G06F 30/20 (2020.01); G06F 17/142 (2013.01); G06F 2111/10 (2020.01); G06F 2113/26 (2020.01)

(58) Field of Classification Search
CPC .... G06F 30/20; G06F 17/142; G06F 2111/10; G06F 2113/26; G06F 17/13; G16C 60/00; G16C 20/10
See application file for complete search history.

(56) References Cited

FOREIGN PATENT DOCUMENTS

| CN | 110222442 A | * | 9/2019 | ............. G06F 30/20 |
| CN | 110660453 A | * | 1/2020 | ............. G16C 10/00 |

(Continued)

*Primary Examiner* — Kandasamy Thangavelu
(74) *Attorney, Agent, or Firm* — Kinney & Lange, P.A.

(57) ABSTRACT

A method and device for simulating microstructure evolution of a material based on solution in an exponential time-difference format. The method includes: establishing a reaction rate theory model for substance defects, wherein the model is expressed with equations that comprise linear terms having coefficients characterized with matrixes; and iteratively solving the equations by using an exponential time-difference format, wherein during the iterative solving, the linear terms with exponential powers of the matrixes as the coefficients are integrated. Since a rate theory is not limited by spatial-temporal scales, the advantages of the rate theory can be significantly reflected when the microstructure evolution is simulated under a high damage dose condition; and (Continued)

then, the equations are solved by using the exponential time-difference format, with a solved result better in accuracy and higher in precision.

10 Claims, 5 Drawing Sheets

(51) Int. Cl.
    *G06F 111/10*     (2020.01)
    *G06F 113/26*     (2020.01)

(56) References Cited

FOREIGN PATENT DOCUMENTS

| | | | | | |
|---|---|---|---|---|---|
| CN | 111914445 | A | * | 11/2020 | ............. G06F 30/23 |
| CN | 112051142 | A | * | 12/2020 | ............... G01N 3/08 |
| CN | 112507539 | A | * | 3/2021 | ............. G06F 30/20 |
| WO | WO 2004079341 | A2 | * | 9/2004 | ......... B29C 45/7693 |

* cited by examiner

SIMULATION OF MICROSTRUCTURE EVOLUTION OF MATERIAL AS SOLVED BASED ON EXPONENTIAL TIME-DIFFERENCE FORMAT

TECHNICAL FIELD

The present invention relates to the computer simulation in physics, and in particular, relates to a method for solving a rate theory equation through parallel computation based on an exponential time-difference format or a method for simulating evolution of a substance by solving based on an exponential time-difference format.

BACKGROUND ART

A microstructure is produced in a material processing process and shows non-uniformity in composition and structure. The microstructure of a material may include spatial distribution phases of different components or crystal structures, crystal grains having different orientations, domains of different structural variants, domains with different electric or magnetic polarizations, and structural defects. These structural features typically have a medium mesoscopic length scale ranging from nanometers to micrometers. The size, shape and spatial arrangement of partial structural features in the microstructure play a crucial role in the aspect of determining the physical properties of a material. A driving force for microstructure evolution pertains to an energy decline of a system. The free energy of the system includes chemical free energy, interfacial energy, elastic strain energy, electromagnetic energy, electrostatic energy, etc.

The microstructure evolution is usually simulated by using a numerical method due to its complexity and non-linearity. In a traditional method for simulating the microstructure evolution, an area for separating component domains or structural domains is regarded as a mathematically sharp interface; a partial interfacial velocity is determined as a part of a boundary condition, or calculated according to the driving force and interfacial mobility of interfacial motion. This relates to the explicit tracking of an interface location. Such an interface tracking method is successful in a one-dimensional system, but becomes impractical for a complex three-dimensional microstructure.

The reaction rate theory is based on the mesoscopic scale simulation of a mean field. In the reaction rate theory, atomic-scale simulation cannot be conducted, but corresponding parameters need to be provided through atomic-scale simulation. At a low spatial-temporal scale, accurate simulation is difficult for the rate theory since it ignores spatial correlation. Therefore, MD/KMC is needed to provide the rate theory with an atomic-scale simulation result. The rate theory relates not only to nucleation but also to growth and coarsening. In general, the molecular dynamics and KMC methods are limited by the spatial-temporal scale. However, the rate theory is not limited by the spatial-temporal scale. Therefore, when the microstructure evolution is simulated under a high damage dose condition, the advantages of the rate theory can be significantly reflected, and a plurality of scales can be involved. Therefore, the reaction rate theory has advantages such as fast computation, high simulated damage dose, and no spatial-temporal and dimensional limitation, and can predict the size distribution and number density of defects for a comparison with an experimental result. So, the reaction rate theory has been widely applied in irradiation-induced microstructure evolution studies, such as irradiation swelling simulation of materials, irradiation growth calculation, cluster precipitation studies, etc.

For a main equation of the rate theory, the Fokker-Plank method is used in a tradition solution, wherein after the main equation is divided, one part is directly solved for the main equation, the other part is subjected to Taylor expansion and then transformed into a Fokker-Plank equation for a solution. However, such a method has the problem of low accuracy.

A phase field model is another microstructure evolution simulation method. The phase field model is originated from the computational materials science and has been widely applied to various processes for simulating the materials physics and computational chemistry. A phase field method has become a highly universal computing method for simulating and predicting mesoscale-level microstructure evolution in the field of computational materials science. The phase field method reflects the comprehensive effect of a physical mechanism by a series of different partial differential equations. Different from a traditional steep interface model, the phase field model, after the concentration is introduced, describes an interfacial area between inner crystal grains of a material in a dispersion interface form, and by the narrow area, the value of internal concentration of the crystal grains gradually evolves into the value of internal concentration corresponding to adjacent crystal grains over time. With this modeling method, the shape change of crystal grains and their movement of an interface location are implicitly determined by the concentration in time, and neither the priori assumption of a structure evolution path of the crystal grains nor the explicit tracking of the interface location of the crystal grains is needed, which greatly simplifies the complexity in simulation computation. This is the greatest advantage of the phase field model, and makes the phase field model applied more and more widely.

However, the phase field model also has a computational problem. Most of the current simulations are performed in two spatial dimensions, and rarely in three dimensions in a large scale. The finite element resolution in the three-dimensional simulation is a computational bottleneck of the verification and prediction based on the phase field method, therefore, the three-dimensional simulation is rarely conducted. An explicit forward Euler formula is used in a traditional solving phase field model, and in order to achieve stability, a time step is necessarily very small in general. This is very costly for the constraint equation of concentration.

SUMMARY OF THE INVENTION

In a first aspect, the embodiments of the present application provide a method for simulating microstructure evolution of a material. The method includes: establishing a reaction rate theory model for substance defects, wherein the model is expressed with equations that comprise linear terms having coefficients characterized with matrixes; and iteratively solving the equations by using an exponential time-difference format, wherein during the iterative solving, the linear terms with exponential powers of the matrixes as the coefficients are integrated.

In an optional implementation, the reaction rate theory model for substance defects may comprise: a point defect concentration equation, a double-defect cluster concentration equation, and a defect cluster concentration equation.

In an optional implementation, the equations comprise non-linear terms; and during the iterative solving, the non-linear terms are numerically solved.

In an optional implementation, during the iterative solving, the non-linear terms are processed by using a predictor-corrector method.

In an optional implementation, said establishing the reaction rate theory model for substance defects comprises: transforming the matrixes to place linear terms diagonally away from the matrixes into the non-linear terms.

In a second aspect, the embodiments of the present application provide a method for simulating evolution of a substance. The method comprises: modeling an evolution process of the substance by using a phase field model to obtain an equation set of an evolution model of the substance, wherein the phase field model comprises high-order spatial derivatives, and the equation set of the evolution model of the substance comprises a substance concentration equation and a phase variable equation; and iteratively solving the equation set of the evolution model, wherein during the iterative solving, the equation set of the evolution model of the substance is transformed; forms of the substance concentration equation and the phase variable equation in a frequency domain are obtained by using a fast Fourier algorithm, including forms of the high-order spatial derivatives in the frequency domain as coefficients of linear terms; the forms of the substance concentration equation and the phase variable equation in the frequency domain are solved by using an exponential time-difference format, and during the solving, the high-order spatial derivatives are accurately solved by using the exponential time-difference format to integrate the linear terms, which take exponential powers of the forms of the high-order spatial derivatives in the frequency domain as the coefficients; and a solved result is subjected to inverse Fourier transform.

In an optional implementation, the phase field model comprises non-linear terms; and during the solving, the non-linear terms are numerically solved.

In an optional implementation, during the solving, the non-linear terms are split and controlled by a linear operator.

In an optional implementation, when the forms of the substance concentration equation and the phase variable equation in the frequency domain are solved by using the exponential time-difference format, multi-step approximation, a Runge-Kutta method or prediction-correction is performed on the non-linear terms to implement the numeric solving.

In a third aspect, the embodiments of the present application provide a computing device. The computing device comprises: at least one memory for storing at least one program; and at least one processor for executing the at least one program stored in the memory, wherein when the at least one program stored in the memory is executed, the processor is configured to execute the method for simulating microstructure evolution of a material as described in the first aspect and the respective embodiments thereof.

In a fourth aspect, the embodiments of the present application provide a computing device. The computing device comprises: at least one memory for storing at least one program; and at least one processor for executing the at least one program stored in the memory, wherein when the at least one program stored in the memory is executed, the processor is configured to execute the method for simulating evolution of a substance as described in the second aspect and the respective embodiments thereof.

In a fifth aspect, the embodiments of the present application provide a computer storage medium storing at least one instruction, wherein the at least one instruction when executed on a computer causes the computer to execute the method as provided in the first aspect.

In a sixth aspect, the embodiments of the present application provide a computer program product containing at least one instruction, wherein the at least one instruction when executed on a computer causes the computer to execute the method as provided in the first aspect.

In a seventh aspect, the embodiments of the present application provide a computer storage medium storing at least one instruction, wherein the at least one instruction when executed on a computer causes the computer to execute the method as provided in the second aspect.

In an eighth aspect, the embodiments of the present application provide a computer program product containing at least one instruction, wherein the at least one instruction when executed on a computer causes the computer to execute the method as provided in the second aspect.

Compared with the prior art, the technical solutions used in the embodiments of the present application as described above have the following technical advantages:

1) The rate theory equation is solved directly by using the exponential time-difference format, with a solved result high in accuracy and good in stability;
2) The established rate model can be solved more rapidly;
3) With the phase field model, neither the priori assumption of a structure evolution path of the crystal grains nor the explicit tracking of the interface location of the crystal grains is needed, which greatly simplifies the complexity in simulation computation; and
4) A computer can be conveniently used for parallel computation, which significantly increases the speed for solving a large-scale equation set.

BRIEF DESCRIPTION OF THE DRAWINGS

The embodiments of the present disclosure can be made clearer by describing the embodiments of the present disclosure in conjunction with the accompanying drawings.

FIG. 3($b$), FIG. 3($d$) and FIG. 3($f$) are schematic diagrams of cluster precipitations and distributions of Cu, Mn and Ni, respectively.

DETAILED DESCRIPTION OF THE INVENTION

Figure 1:
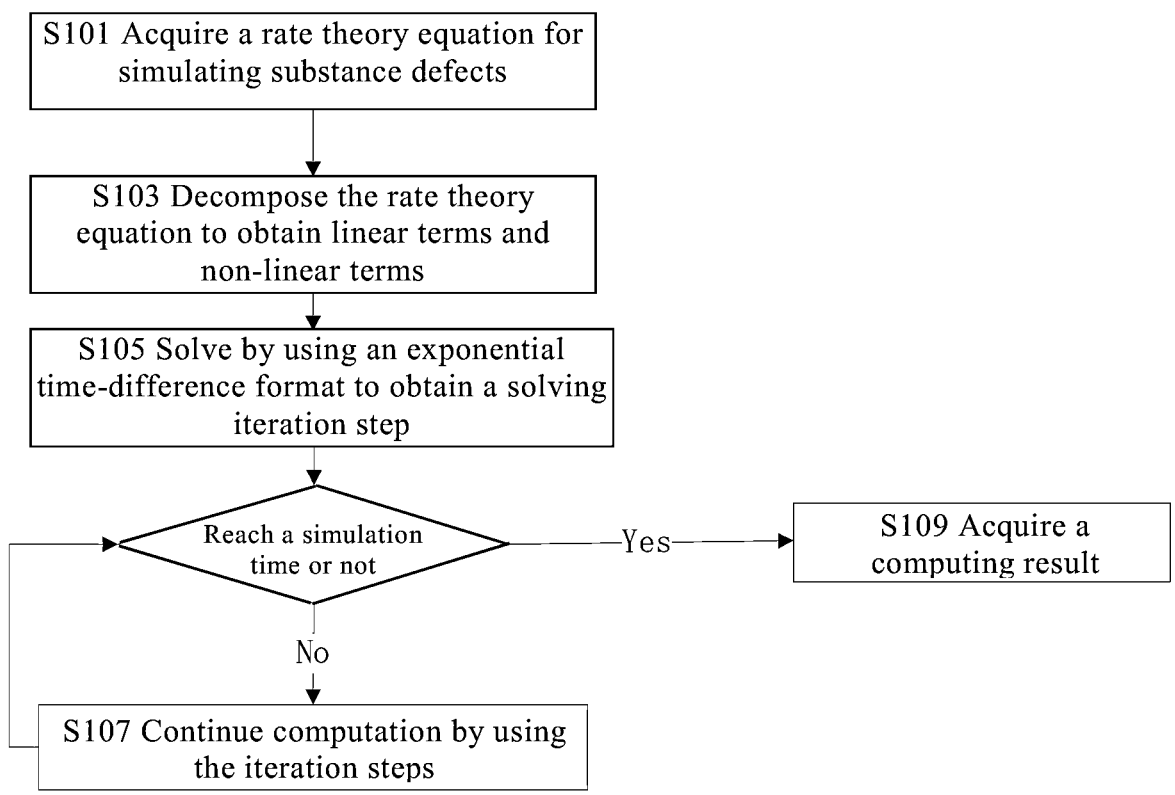
FIG. 1 is a flow chart of a computational part of a method for solving a rate theory equation through parallel computation based on an exponential time-difference format according to an embodiment of the present application.

The embodiments of the technical solutions of the present invention will be described in detail below in conjunction with the accompanying drawings.

It should be noted that, unless otherwise specified, the technical terms or scientific terms used in the present application should have the ordinary meanings as understood by those killed in the art of the present invention.

Exponential integral operations are reserved in the exponential time-difference format, where the integrals of the integrating factor terms and non-linear terms of a target equation in time are processed differently. In an exponential time-difference method, a non-linear term in an equation is approximated by using polynomial interpolation, and then, a generated new integral term is integrated accurately. The exponential time-difference method is conductive to meet the requirements in the aspects of improving the precision and increasing the time step for the material microstructure evolution simulation including the reaction rate theory and the phase field model.

Embodiment 1 Solving of Rate Theory Equations

In this embodiment, a reaction rate theory model for substance defects is established, and an equation set to be solved is determined; and the established equation set of the reaction rate theory model for substance defects is solved by using an exponential time-difference method.
Part I Reaction Rate Theory Model A model is established based on a reaction rate theory because the reaction rate theory has advantages such as fast computation, high simulated damage dose, and no spatial-temporal and dimensional limitation, and can predict the size distribution and number density of substance microscopic defects. Specifically, the rate theory is based on the mesoscopic scale simulation of a mean field, and does not need atomic scale simulation itself, as long as some of the parameters are provided based on the atomic scale simulation. In general, the molecular dynamics and KMC methods are limited by the spatial-temporal scale. However, the rate theory is not limited by the spatial-temporal scale. Therefore, when the microstructure evolution is simulated under a high damage dose condition, the advantages of the reaction rate theory can be significantly reflected.

In an embodiment, the reaction rate theory model for substance defects may include: a point defect concentration equation, a double-defect cluster concentration equation, and a defect cluster concentration equation. A solution C in the equation represents the number density of defects of different sizes.

The point defect concentration equation may be expressed as follows by using interstitial defects:

$$\frac{dC_{1i}}{dt} = G_{1i} - R_{iv}C_{1i}C_{1v} - K_{1i}C_{1i} - 4\beta_{1i}^i C_{1i}C_{1i} + \\ 4\alpha_{2i}^i C_{2i} + \beta_{2i}^v C_{1v}C_{2i} - C_{1i}\sum_{n=2}\beta_{ni}^i C_{ni} + \sum_{n=3}\alpha_{ni}^i C_{ni} - C_{1i}\sum_{n=2}\beta_{nv}^i C_{nv} \quad (1)$$

In this equation, a first term indicates a defect generation terms G; a second term indicates a defect combination term; a third term represents a defect tail-end term; a fourth term represents a concentration decrease (of single interstitial atoms (SIA)) caused by the absorption of (SIA) by SIA; a fifth term indicates a release interstice between two interstices; a sixth term represents a concentration decrease of (VAC) caused by the absorption of (VAC) by the SIA; a seventh term represents the absorption of an interstice by a plurality of interstices; an eighth term represents a concentration increase (of SIA) caused by the release of (SIA) (by nSIA); and a ninth term corresponds to the absorption of an interstice by a plurality of vacancies. During implementing, the defect generation term G is unified in unit in order to ensure the unity of the unit.

In this equation, c indicates the number density of defects of different sizes; i represents an interstice; l represents the number of the interstice; R indicates a defect combination rate; K includes the effect of a dislocation/crystal boundary on the interstice and vacancy; and a and R represent the absorption rate and the release rate at which n vacancy or interstitial atoms absorb or release one vacancy or interstitial atom, respectively.

The point defect concentration equation may be expressed as follows by using vacancy defects:

$$\frac{dC_{1v}}{dt} = G_{1v} - R_{iv}C_{1i}C_{1v} - K_{1v}(C_{1v} - C_v^e) - 4\beta_{1v}^v C_{1v}C_{1v} + \\ 4\alpha_{2v}^v C_{2v} + \beta_{2v}^i C_{1i}C_{2v} - C_{1v}\sum_{n=2}\beta_{nv}^v C_{nv} + \sum_{n=3}\alpha_{nv}^v C_{nv} - C_{1v}\sum_{n=2}\beta_{ni}^v C_{ni} \quad (2)$$

In this equation, the corresponding relations of respective terms are consistent with those in the equation (1), except that the interstices are substituted by vacancies, v represents a vacancy, and 1 represents the number of vacancies, the details of which will not be repeated here again.

For the equation of interstices, the reason why $(C_{1i} - C_i^e)$ is not considered lies in that the thermal equilibrium concentration of interstitial atoms $C_i^e$ in a material is far lower than the thermal equilibrium concentration $C_v^e$ of the vacancies, and meanwhile, the interstitial atoms are very difficult to release due to the sink strength of dislocations and the like. Therefore, $(C_{1v} - C_v^e)$ is considered only in the equation of vacancies.

In the equation above, K includes the effect of a dislocation/crystal boundary on the interstice and vacancy. The mathematic formulas of K are as follows:

$$K_{1i} = Z_i^d \rho_d D_i + \frac{6D_i\sqrt{Z_i^d \rho_d + \frac{\left(C_{1i}\sum_{m=2}^{Nid}\beta_{mi}^i C_{mi} + C_{1i}\sum_{m=2}^{Nvd}\beta_{mv}^i C_{mv}\right)}{D_i}}}{\text{Grain}} + \\ C_{1i}\sum_{m=2}^{Nid}\beta_{mi}^i C_{mi} + C_{1i}\sum_{m=2}^{Nvd}\beta_{mv}^i C_{mv} \quad (3)$$

$$K_{1v} = Z_v^d \rho_d D_v + \frac{6D_v\sqrt{Z_i^d \rho_d + \frac{\left(C_{1v}\sum_{m=2}^{Nid}\beta_{mi}^v C_{mi} + C_{1v}\sum_{m=2}^{Nvd}\beta_{mv}^v C_{mv}\right)}{D_v}}}{\text{Grain}} + \\ C_{1v}\sum_{m=2}^{Nid}\beta_{mi}^v C_{mi} + C_{1v}\sum_{m=2}^{Nvd}\beta_{mv}^v C_{mv} \quad (4)$$

K in the formulas consists of three terms, including the sink strengths of a dislocation loop, a dislocation, and a crystal boundary. $D_i$ and $D_v$ represent the diffusion coefficients of different types of defects; $Z_i^d$ and $Z_v^d$ represent constants related to p; and p represents the dislocation density.

The double-defect concentration equation may be expressed as follows by using interstitial defects (Formula (5)) or vacancy defects (Formula (6)):

$$\frac{dC_{2i}}{dt} = 2\beta_{1i}^i C_{1i}^2 - 2\alpha_{2i}^i C_{2i} - \beta_{2i}^i C_{1i}C_{2i} + \alpha_{3i}^i C_{3i} - \beta_{2i}^v C_{1v}C_{2i} + \beta_{3i}^v C_{1v}C_{3i} \quad (5)$$

-continued $$\frac{dC_{2v}}{dt} = 2\beta_{1v}^{v}C_{1v}^{2} - 2\alpha_{2v}^{v}C_{2v} - \beta_{2v}^{v}C_{1v}C_{2v} + \alpha_{3v}^{v}C_{3v} - \beta_{2v}^{i}C_{1i}C_{2v} + \beta_{3v}^{i}C_{1i}C_{3v} \quad (6)$$

Since only one point defect of double defects is movable, i.e., divergentable or absorbable, the double-defect concentration equation only includes 6 terms, and the concentration changes of the double defects are related to one, two or three interstices, or one, two or three vacancies. The processing to the equation here belongs to the common knowledge in the art, the details of which will not be repeated here again.

The defect cluster concentration equation may be expressed as follows by using interstitial defects (Formula (7)) or vacancy defects (Formula (8)):

$$\frac{dC_{ni}}{dt} = (\beta_{(n-1)i}^{i}C_{1i})C_{(n-1)i} + \quad (7)$$
$$(\beta_{(n+1)i}^{v}C_{1v} + \alpha_{(n+1)i}^{i})C_{(n+1)i} - (\alpha_{ni}^{i} + \beta_{ni}^{v}C_{1v} + \beta_{ni}^{i}C_{1i})C_{ni}$$

$$\frac{dC_{nv}}{dt} = (\beta_{(n-1)v}^{v}C_{1v})C_{(n-1)v} + \quad (8)$$
$$(\beta_{(n+1)v}^{i}C_{1i} + \alpha_{(n+1)v}^{v})C_{(n+1)v} - (\alpha_{nv}^{v} + \beta_{nv}^{i}C_{1i} + \beta_{nv}^{v}C_{1v})C_{ni}$$

In these equations, α and β respectively represent the absorption ratio and release ratio at which n vacancy or interstitial atoms absorb or release one vacancy or interstitial atom.

For a further explanation, Formula (1) and Formula (2) express an equation having one point defect, Formula (5) and Formula (6) express an equation having two point defects, and Formula (7) and Formula (8) express an equation having more than three point defects, i.e., 3 to n point defects.

Part II Solving of the Equations of the Established Rate Theory Model for Substance Defects 1) The equations to be solved are decomposed into linear terms and non-linear terms.

A thought for decomposition is as follows: all the variables in the equations above are saved in a matrix form; and the equations above include many linear terms and non-linear terms. In an example, for example, the linear terms are allowed to be distributed near a diagonal line of a coefficient matrix through matrix transformation as far as possible, and the terms far away from the diagonal line are not placed in the coefficient matrix, but in another matrix together with the non-linear terms.

2) The linear and non-linear terms obtained from the decomposition above are solved by using the exponential time-difference format to obtain a solution to an ordinary differential equation set.

In an example, an iterative equation obtained by solving in the exponential time-difference format is as follows, and then, the iterative equation is used for computation to obtain a final solution to the equation. The equation described here may be either the point defect concentration equation, or the double-defect cluster concentration equation and the defect cluster concentration equation.

$$C_{n+1} = C_n \cdot e^{\Delta t \cdot L} + FC \cdot \Delta t \cdot \frac{e^{\Delta t \cdot L} - 1}{\Delta t \cdot L}$$

In this equation, $C_n$ indicates the number density of defects under the $n^{th}$ iteration; L indicates the linear terms obtained through the decomposition, FC indicates the non-linear terms and the remaining linear terms after the decomposition, and $\Delta t$ indicates a time length of simulation of each iteration step. A predictor-corrector method may be used for processing during solving, and the iteration is performed by using the iterative equation until a cumulative result of $\Delta t$ reaches the time length of simulation as required. At this point, C obtained is the final solution to the equation set, and this final solution includes the number densities of the vacancy and interstitial atoms at different scales.

A linear part containing high-order derivatives in the equation is separated from a non-linear part (2.12) containing partial free energy density, interfacial energy anisotropy and elastic strain energy.

For the convenience of understanding, a derivation process generated from the iterative equation is as follows. Equation (5) here is explained as an example, and other equations have similar derivation process.

$$\frac{dC_{2i}}{dt} = 2\beta_{1i}^{i}C_{1i}^{2} - 2\alpha_{2i}^{i}C_{2i} - \beta_{2i}^{i}C_{1i}C_{2i} + \alpha_{3i}^{i}C_{3i} - \beta_{2i}^{v}C_{1v}C_{2i} + \beta_{3i}^{v}C_{1v}C_{3i}$$

For the convenience of description, the equation is transformed here, and meanwhile, the variables therein are substituted by using other variables.

$$\frac{dC_{2i}}{dt} = L \cdot C_{2i} + Fc$$

In this equation, $L = -2\alpha_{2i}^{i}$, $Fc = 2\beta_{1i}^{i}C_{1i}^{2} - \beta_{2i}^{i}C_{1i}C_{2i} + \alpha_{3i}^{i}C_{3i} - \beta_{2i}^{v}C_{1v}C_{2i} + \beta_{3i}^{v}C_{1v}C_{3i}$.

The solving for the equation above is equivalent to the solving of the equation below:

$$\frac{d}{dt}(e^{-Lt} \cdot C_{2i}) = Fc \cdot e^{-Lt}$$

The equation above are integrated from $t_n$ to $t_{n+1}$, to obtain:

$$C_{2i}(t_{n+1}) = C_{2i}(t_n) \cdot e^{Lh} + \int_{t_n}^{t_{n+1}} Fc \cdot e^{L(t_{n+1}-t)} dt$$

In this equation, $t_{n+1} = t_n + h$, ie., $h = \Delta t$. Let $t = t_n + \tau$, and the equation above may be transformed as follows:

$$C_{2i}(t_{n+1}) = C_{2i}(t_n) \cdot e^{Lh} + e^{Lh} \int_{0}^{h} Fc \cdot e^{-L\tau} d\tau$$

The integrated parts are numerically approximated (for example, polynomially approximated) to obtain a numeric format of the rear integrated part, thereby obtaining an iterative equation of the exponential time-difference format.

$$C_{2i}(t_{n+1}) = C_{2i}(t_n) \cdot e^{Lh} + L^{-1}(e^{Lh} - 1) \cdot Fc$$

Each equation is solved in such a way, and then all the equations are placed in the matrix to obtain a final iterative equation below:

$$C_{n+1} = C_n \cdot e^{\Delta t \cdot L} + Fc \cdot \Delta t \cdot \frac{e^{\Delta t \cdot L} - 1}{\Delta t \cdot L}$$

It should be pointed out that the concentration equations with the respective defect numbers above may be combined into a matrix equation. At this point, k in the concentration equations with different defect numbers may form one k-number matrix.

In an example, the predictor-corrector is used during the iteration:

The iterative equation above is solved to obtain a first approximation value, which is referred to as a predicted value. The predication precision at this point may be low, therefore, the iterative equation may be used again and corrected once to obtain a corrected value.

$$C_{n+1} = C_n \cdot e^{\Delta t \cdot L} + (Fc_1 - Fc_0) \cdot \Delta t \cdot \frac{e^{\Delta t \cdot L} - 1}{\Delta t \cdot L}$$

In addition, during the solving, each variable is saved in a matrix form, which is very beneficial to parallel processing. In an example, when a computer is used for the parallel processing, each processing unit may process its data in parallel, and the communication is needed only when the data of other units is needed. By observing the equation set to be solved, it can be seen that each solving unit always needs to communicate with two adjacent computing units. In another example, during the solving of the point defect concentration equation by a computer, a cumulative summation value needed to be broadcast to each computing unit.

FIG. 1 is a flow chart of a computational part of a method for solving a rate theory equation through parallel computation based on an exponential time-difference format according to the present invention, with the steps as follows:

In Step S101, a rate theory model for substance defects is acquired. The model includes a point defect concentration equation, a double-defect cluster concentration equation, and a defect cluster concentration equation.

In Step S103, the rate theory equation set is decomposed to obtain linear terms and non-linear terms; and an exponential time-difference format is constructed based on the linear terms and the non-linear terms.

In Step S105, the decomposed rate theory equation set is solved by using the exponential time-difference format to obtain a unified solving iteration step.

In Step S107, the simulated time is judged. If the simulated time is not reached, the solving iteration step is used to proceed with the computation of a next time, i.e., an equation solution of a next iteration; and the simulated time is advanced by one iteration.

If the simulated time is reached, a next step is performed.

In Step S109, a computed solution of the model as obtained from the process above is provided to end the computation. The solution includes the number densities of vacancy atom and interstitial atoms at different scales, i.e., the solving purpose of the model.

As can be seen from above, the method for solving the rate theory equation through parallel computation based on the exponential time-difference format according to the embodiments of the present application has the following advantages: the rate theory is used without any spatial-temporal scale limitations, and when the microstructure evolution is simulated under a high damage dose condition, a plurality of scales can be involved, and the size distribution and number density of defects can be predicted rapidly; the rate theory equation is solved directly by using the exponential time-difference format, with a solved result high in accuracy and good in stability; the established rate model can be solved more rapidly; the established rate model can be solved more rapidly; and a computer can be conveniently used for parallel computation, which significantly increases the speed for solving a large-scale equation set.

Embodiment 2 Method for Simulating Evolution of Substance

In this embodiment, the method for simulating the evolution of a substance is combined with the phase field model and the exponential time-difference format. A phase field equation has the characteristics of high-order spatial derivatives and strong non-linearity, so that a time sub-step is limited. The exponential time-difference format may be used for precisely solving the high-order spatial derivatives, and the non-linear terms may be split and controlled by a linear operator so that the overall algorithm format is stable. In this way, a time step being two magnitude-order higher than that in a traditional method can be used for computation. In addition, the exponential time-difference format is naturally adaptive to a parallel domain decomposition method, which can be better utilized by using a finite-element spatial-dispersion compact exponential time-difference format.

In the method for simulating the evolution of a substance according to this embodiment, a substance evolution environment to be simulated is modeled; and the equations of a substance evolution model as obtained through modeling are solved to obtain a solution which is a change process and result of substance evolution.

Part I Modeling of Substance Evolution to be Simulated

When the substance evolution environment to be simulated is modeled, physical factors that need to be incorporated into the consideration of this model are determined, and the selection on the type of a physical-mathematical model is determined for describing the substance evolution environment to be simulated.

In this embodiment, a substance evolution process is modeled by using a phase field model, in which the shape change of crystal grains and their movement at an interface location are implicitly determined by the concentration in time, and neither the priori assumption of a structure evolution path of the crystal grains nor the explicit tracking of the interface location of the crystal grains is needed, which greatly simplifies the complexity in simulation computation. This is the greatest advantage of the phase field model.

The process of phase field simulation is constrained by energy. Therefore, energy terms in this model may be correspondingly modified to control a simulation process. For example, a flexible term may be added to the energy terms to add a flexible constraint to a simulation process.

A phase field is used as a tool for simulating the substance evolution process, in which an equation set is mainly solved. The equation set includes two dynamic equations, which are common in related literature and serve as a basis of the basic physics of the phase field model. Specifically, in a phase field method, the evolution processes of different concentrations over time are controlled by a series of different partial differential equations, with one partial differential equation corresponding to one concentration. These partial differential equations are typically derived from the principle of non-equilibrium thermodynamics corresponding to the system, for the purpose of ensuring that system components are in line with the conservation of mass while the total free energy of the system decreases along with the evolution over time.

In an example, an equation set of the substance evolution model based on the phase field model is as follows:

$$\begin{cases} \dfrac{\partial c_i(r,t)}{\partial t} = \nabla \cdot M_i \cdot \nabla \dfrac{\partial F}{\partial c_i(r,t)} \\ \dfrac{\partial \eta(r,t)}{\partial t} = -L_\eta \dfrac{\partial F}{\partial(\eta,t)} \end{cases}$$

In this equation set, $c_i$ indicates substance concentration; $\eta$ indicates a phase variable; r indicates a position; t indicates time; F indicates the free energy of the system; $M_i$ indicates the mobility of different substances; and $L_\eta$ indicates dynamic mobility that characterizes the phase evolution between phases a and $\gamma$.

These two equations constrain the substance concentration and the phase variable respectively.

In the equation set above, F may be defined as $$F = \int_V \left\{ [1 - \eta^2(3-2\eta)] \left( G_c^\alpha(c_i,T) + YV_m \varepsilon_0^2(c_i) \right) + \right.$$

$$\left. \eta^2(3-2\eta)G_c^\gamma(c_i,T) + W\eta^2(1-\eta)^2 + \sum_{i=1}^{4} \frac{1}{2} k_c(\nabla c_i)^2 + \frac{1}{2} k_\eta(\nabla \eta)^2 \right\} dv$$

$M_i$ physically means the ability of alloy elements to diffuse and transition. The higher the $M_i$, the faster and farther the diffusion of the alloy elements. $M_i$ changes constantly over iteration, and $M_i$ may be defined as follows:

$$M_i(\eta,T) = c_{oi}(1-c_{oi}) \times \left\{ (1-\eta)\frac{D_i^\alpha(T)}{RT} + \eta \frac{D_i^\gamma(T)}{RT} \right\}$$

In the definitions of F and $M_i$, $k_c$ and $k_\eta$ indicate gradient energy coefficients; $V_m$ indicates a molar volume; R indicates a gaseous constant; T indicates temperature; $D_i^\alpha$ and $D_i^\gamma$ indicate a diffusion coefficients; $G_c^\alpha$ and $G_c^\gamma$ indicate gibbs free energy; and Y indicates average stiffness.

Part II Solving of Equations of Substance Evolution Model

When the established substance evolution model is solved, the original equation is first transformed into a form suitable for solving in the exponential time-difference format; next, the transformed equation or the equation of the evolution model with a form in the spatial domain is subjected to fast Fourier transform to obtain a form of the equation of the evolution model in the frequency domain; then a solution to the equation with the form in the frequency domain is obtained; inverse Fourier transform is performed on the solution in the frequency domain; and finally, the solution to the original equation, i.e., the solution to the evolution model in the form in the spatial domain, is obtained. This method is essentially to transform the mathematically continuous solving into the discrete solving on a computer.

That is, a strategy of accumulating minimal values is used on the computer, and during the solving, constant iteration and correction are performed to approach the result.

The method for simulating the evolution of the substance according to the present embodiment is characterized in that for the result obtained after the fast Fourier transform, the equation of the iteration step in the frequency domain is solved for the evolution model by using the exponential time-difference format, and then, the equation of the iteration step is used to achieve a solution of the evolution model in the frequency domain. Solving in such a way is fast with high accuracy and good stability, and the computer can be used conveniently for parallel computation, which is more conductive to the solving of a large-scale equation set.

The method for simulating the evolution of the substance according to this embodiment is additionally characterized in that the solving process is constantly transformed alternatively between the forms in the spatial domain and the frequency domain of the model equations. The reason is that the substance mobility in the established evolution model cannot be processed as a constant and changes constantly in each step of iteration of the substance evolution; and the substance mobility is affected by a phase variable, and both the substance mobility and the phase variable need to be solved in the spatial domain of the equation. Therefore, for each iteration, these two values need to be solved by returning to the spatial domain, which is then changed to the frequency domain for achieving a solution, and the iteration may not be performed with the iteration equation of the frequency all the time.

In an example, a specific solving method is discussed below.

1) The equations of the substance evolution model are transformed so that they can be appropriately solved by using the exponential time-difference format after the Fourier transform. For example, the substance concentration equation may be transformed with the steps below. In this formula, a splitting parameter C is introduced for ensuring an energy decrease process during the solving.

$$\frac{\partial c_i(r,t)}{\partial t} = -\left(C\Delta^2 c_i - k\Delta c_i\right) + \nabla \cdot (M_i) \cdot \nabla(f(c_i) - \Delta c_i) + C\Delta^2 c_i - k\Delta c_i \quad (9)$$

$$\frac{\partial c_i(r,t)}{\partial t} = -\left(C\Delta^2 c_i - k\Delta c_i\right) + g(c_i)$$

The phase variable equation may be transformed in a similar fashion, the details of which will not be repeated here.

2) The equation set of the substance evolution model is performed fast Fourier transform so as to make a preparation for solving in the frequency domain. Since the substance mobility $M_i$ changes in each iteration during the evolution and may not be processed as a constant, $M_i$ should be solved at first in each iteration; and moreover, since the $M_i$ changes with the phase variable $\eta$ during the iteration, the phase variable $\eta$ needs to be solved at first according to the phase variable equation before solving $M_i$, and then, a $\nabla$.

$$M_i \cdot \nabla \frac{\partial F}{\partial c_i(r,t)}$$

part of the current iteration is computed according to the obtained phase variable $\eta$, after which the fast Fourier transform may be performed on the substance concentration equation and the phase variable equation.

The purpose of performing the Fourier transform is to achieve a solution in the frequency domain, thereby solving the formulas of iteration steps in the frequency domain for the substance concentration equation and the phase variable equation.

3) The content following the Fourier transform is solved by using the exponential time-difference format to obtain a formula of iteration step corresponding to the frequency domain of each equation, and then, a solution in the frequency domain is achieved according to the obtained iteration formula.

The corresponding iteration step of the solved substance concentration equation in the frequency domain is mathematically expressed as follows:

$$\widehat{C_{n+1}} = \widehat{C_n} \times e^{-\Delta t \times K_4 \times Cc} - (grcoef_C \times \widehat{Cx} - \widehat{dgdC}x - Cc \times K_4 \times \widehat{C_n}) \times \left(\frac{1 - e^{-\Delta t \times K_4 \times Cc}}{Cc \times K_4}\right)$$

In this equation, C indicates a corresponding substance concentration; $grcoef_C$ indicates a parameter related to the substance; $C_c$ indicates an adjusting coefficient; $K_4$ indicates a result obtained after the Fourier transform of $\Delta^2$; Cx and dgdCx indicate results obtained after computing terms in $$\frac{\partial F}{\partial c_i(r,t)}$$

and $M_i$; and the symbol $\widehat{\phantom{x}}$ indicates a corresponding result after the Fourier transform.

The iteration step of the phase variable equation in the frequency domain may be conveniently obtained, with a mathematical expression as follows:

$$\widehat{orp_{n+1}} = \widehat{orp_n} \times e^{-\Delta t \times K_2 \times mcoef_{orp}} - \widehat{dgdo}r \times mcoef_{orp} \times \left(\frac{1 - e^{(-\Delta t \times K_2 \times mcoef_{orp})}}{mcoef_{orp} \times K_2}\right)$$

In this equation, orp indicates a phase variable; $mcoef_{orp}$ indicates mobility related to the substance; $C_c$ indicates an adjusting parameter; $K_2$ indicates a result obtained after the Fourier transform of $\nabla$; and dgdor indicates a result obtained after computing terms in $$\frac{\partial F}{\partial c_i(r,t)}.$$

Since the phase variable has no part similar to $M_i$ that must be solved in the spatial domain, the iteration equation as required may be obtained very conveniently.

Moreover, in Formula (9), after the Fourier transform and the solving with exponential time-difference, $-(C\Delta^2 c_i - k\Delta c_i)$ will correspond to $\widehat{C_n} \times e^{-\Delta t \times K_4 \times C}$ in the iteration equation; and after the Fourier transform and the solving with the exponential time-difference, $g(c_i) = \nabla \cdot (M_i) \cdot \nabla (f(c_i) - \Delta c_i) + C\Delta^2 c_i - k\Delta c_i$ will correspond to $(grcoef_c \times \widehat{Cx} - \widehat{dgdC} x - C_c \times K_4 \times \widehat{C_n} + k \times K_2 \times \widehat{C_n})$ in the iteration equation.

Accordingly, after the Fourier transform and the solving with the exponential time-difference, $C\Delta^2 c_i - k\Delta c_i$ in the phase variable equation corresponds to $Cc \times K_4 \times \widehat{C_n} + k \times K_2 \times \widehat{C_n}$; and $\nabla - (M_i) \cdot \nabla (f(c_i) - \Delta c_i)$ corresponds to $grcoef_c \times \widehat{Cx} - \widehat{dgdC} x$.

In a method for the exponential time-difference, the high-order derivative terms in the phase field equation are accurately integrated by using an integrating factor; the non-linear part of the equation is solved by using multi-step approximation, a Runge-Kutta method, a predictor-corrector method and the like to obtain a numeric solving format of the phase field equation; and by using an operator splitting format, the energy stability of a solving format is guaranteed.

Based on the iteration steps corresponding to the frequency domains of the substance concentration equation and the phase variable equation as described above, it can be very convenient to achieve a solution in the frequency domain for the current iteration of the substance concentration equation and the phase variable equation.

4) The solutions in the frequency domain as achieved for the current iteration of the substance concentration equation and the phase variable equation in the step described above are subjected to the inverse Fourier transform, to achieve a solution (i.e., the solution in the spatial domain) to the substance concentration equation and the solution (i.e., the solution in the spatial domain) to the phase variable equation for the current iteration.

The solution to the substance concentration equation and the solution to the phase variable equation, namely the value of substance concentration and the value of phase variable at the current time, are saved, wherein the value of substance concentration may describe a process state of a change in the substance evolution.

5) The steps 2) and 3) are cycled till the required number of iteration steps (i.e., the required evolution time) are reached, and the value of substance concentration at the current time is obtained, which may describe a result of the substance evolution.

In addition, in the solving process described above, it can be seen that each variable is saved in a matrix form, which is very beneficial to the parallel processing on a computer and may be used to decompose data. In this way, a plurality of data processing units may process part of their data in parallel at the same time, and communicate with other processing units only when other processing units are needed for data processing. In an embodiment, the cases in which the data processing units need to communicate with other processing units include: when the edge data of the matrix is processed in a process of solving $\nabla \cdot M_i \cdot \nabla$, the gradient and divergence of the edge data are related to adjacent matrixes and processing units, so that the communication with the adjacent matrixes and processing units is needed to obtain a required value.

Figure 2:
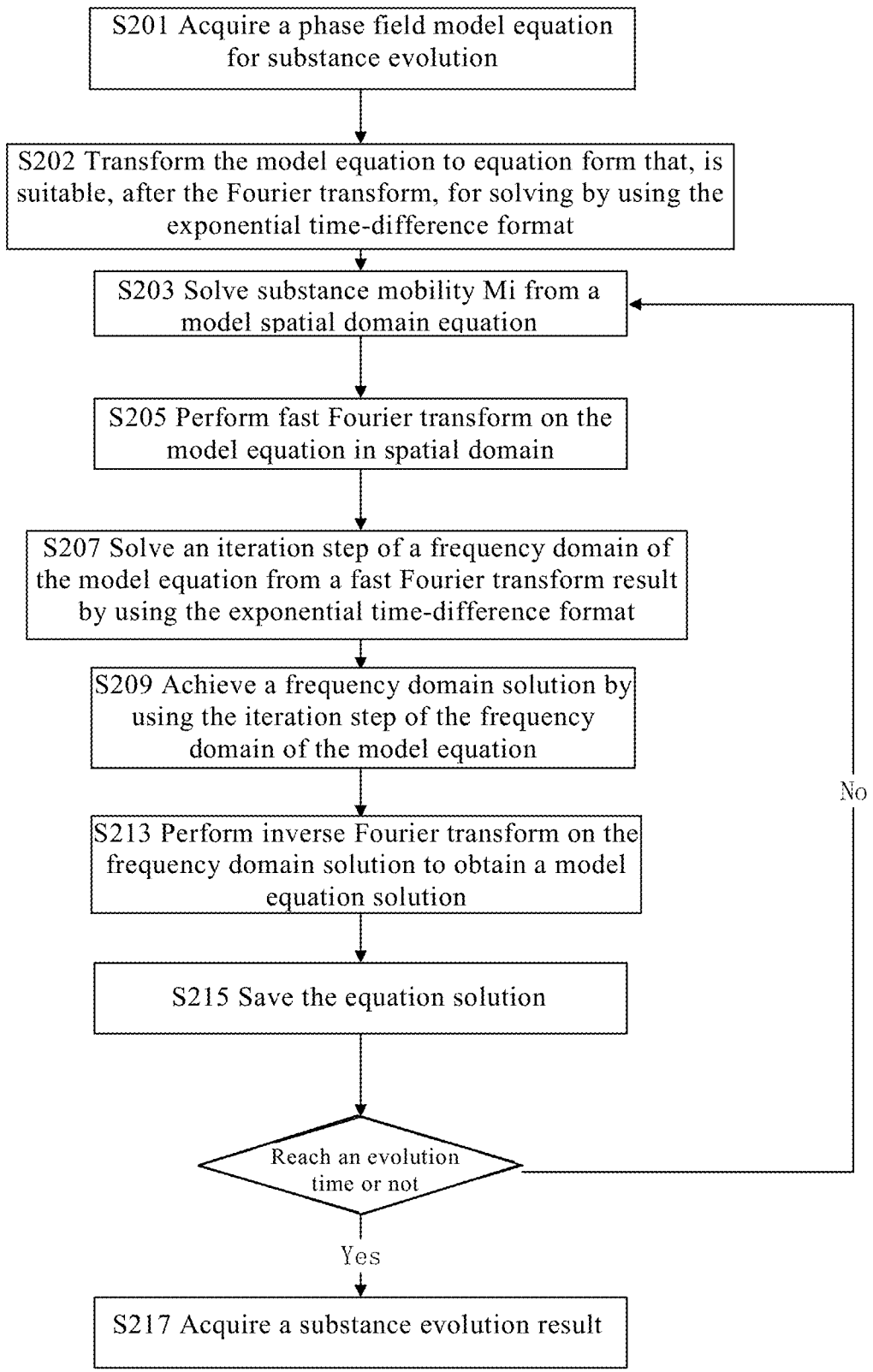
FIG. 2 is a flow chart of a computational part of a method for simulating evolution of a substance by solving based on an exponential time-difference format according to an embodiment of the present application.
Figure 3A:
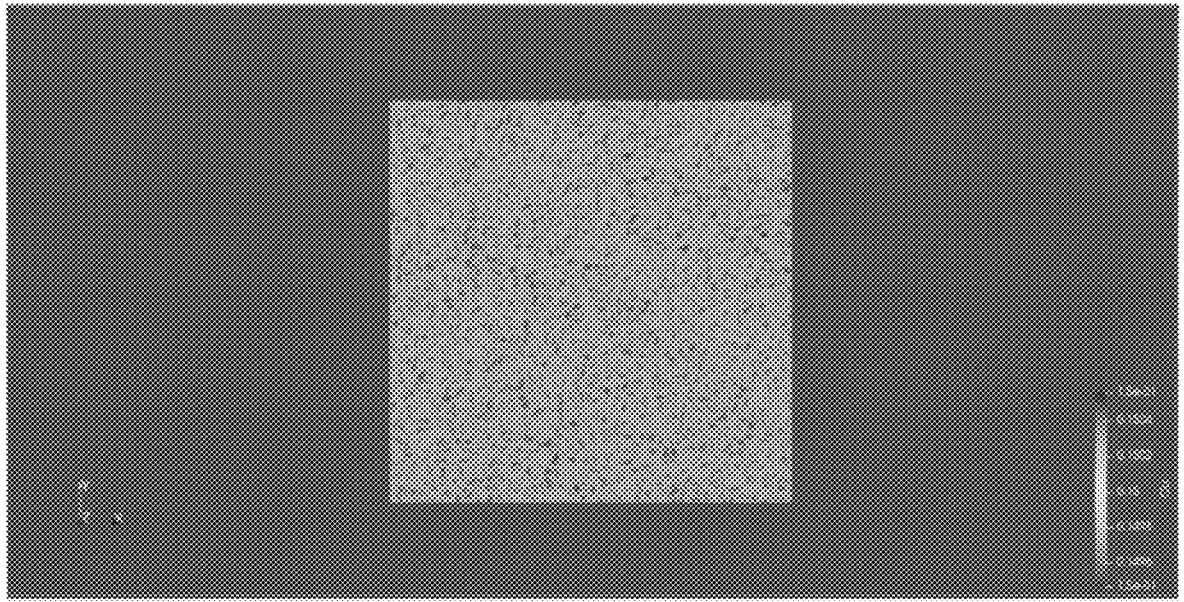
FIGS. 3($a$)-3($f$) shows Cu cluster precipitation after 15,000 steps when an alloy has a composition of Fe—Cu—Mn—Ni, wherein FIG. 3($a$), FIG. 3($c$) and FIG. 3($e$) are schematic diagrams of initial distributions of Cu, Mn and Ni, respectively.
Figure 3B:
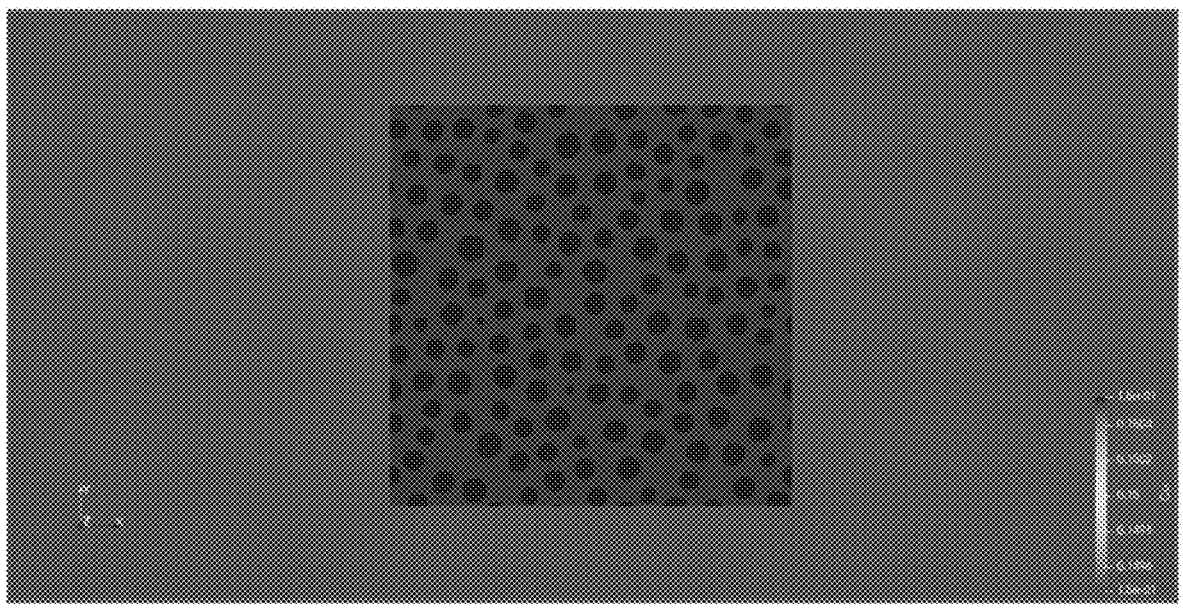
Figure 3C:
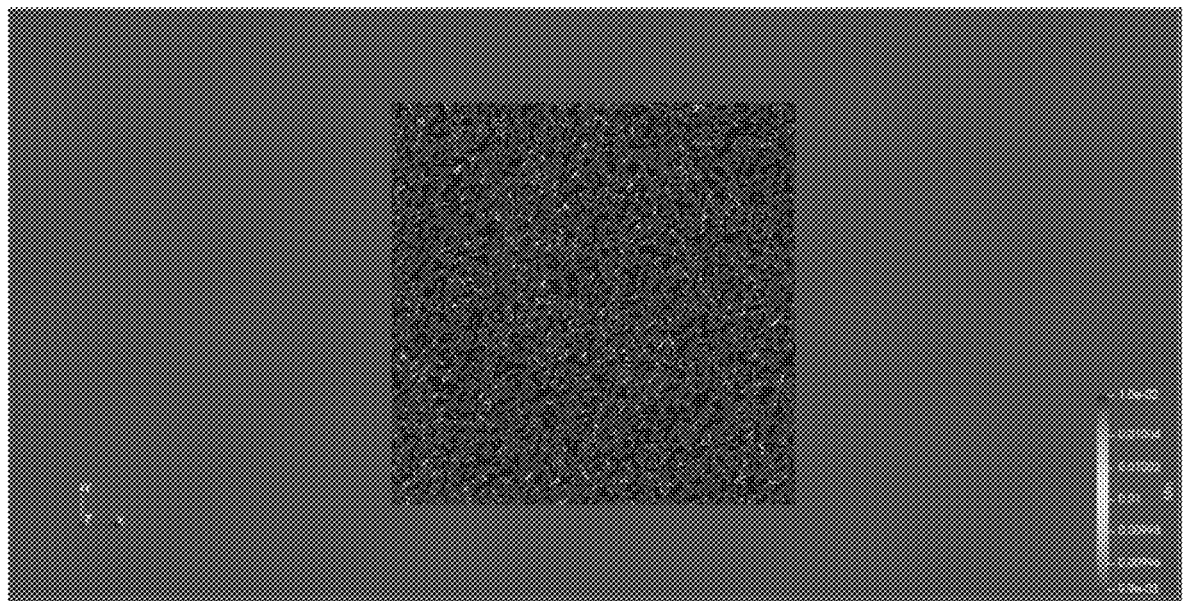
Figure 3D:
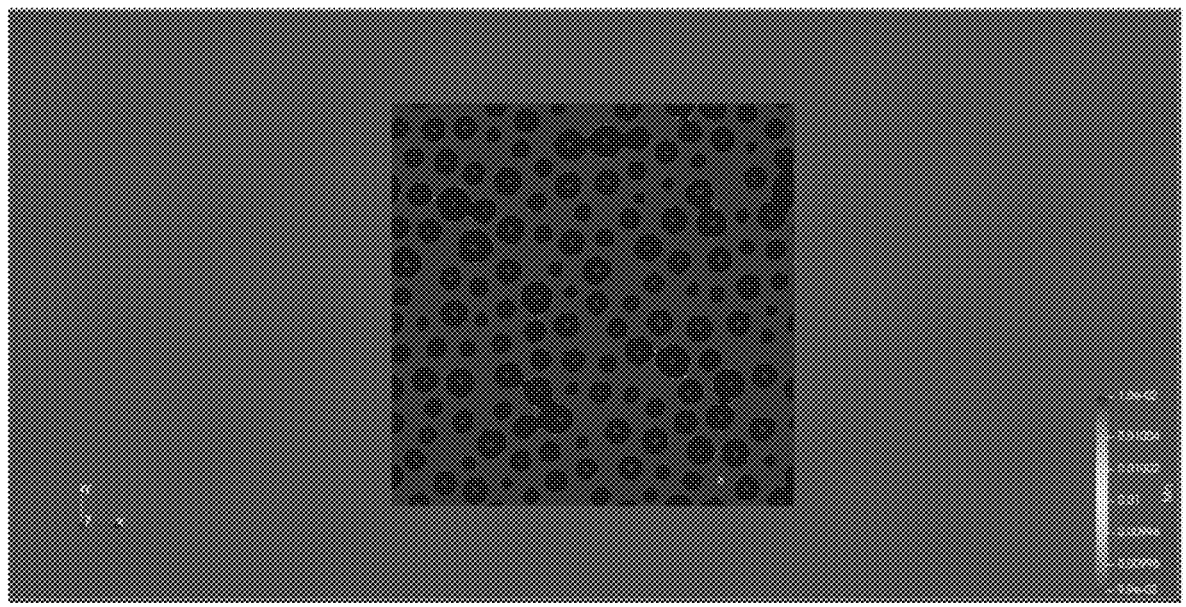
Figure 3E:
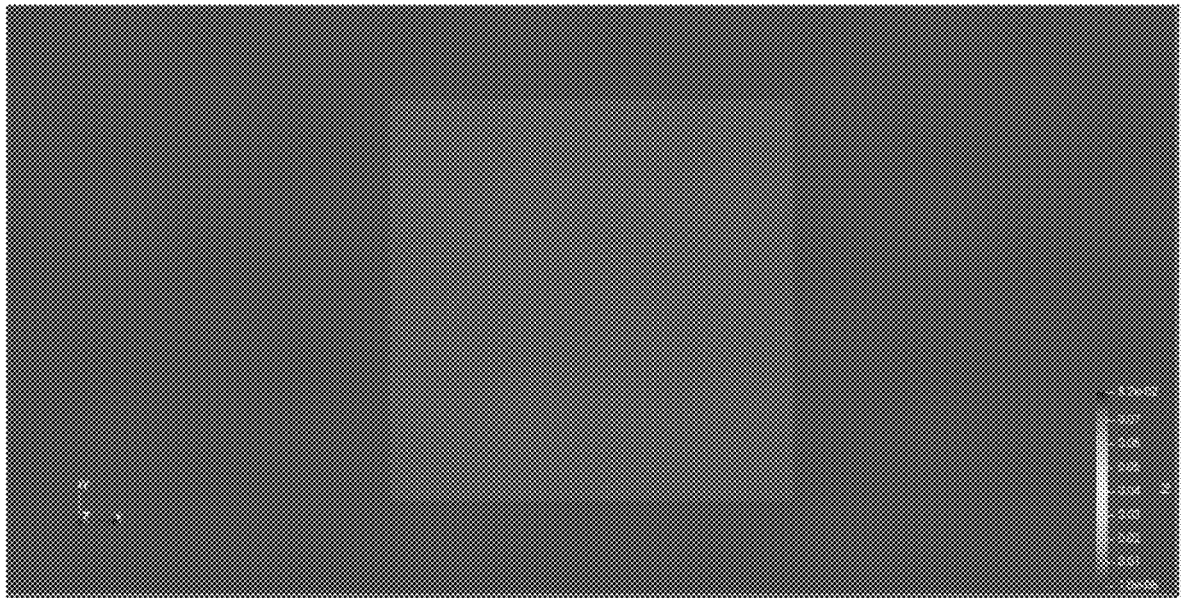
Figure 3F:
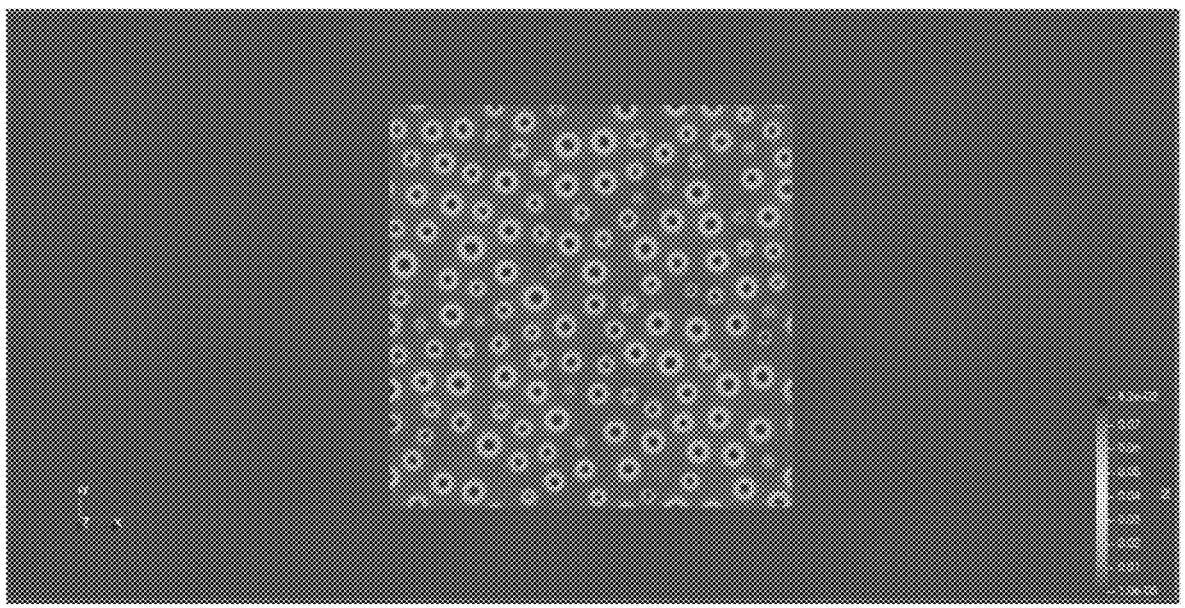

FIG. 2 is a flow chart of a computational part of a method for simulating evolution of a substance by solving based on an exponential time-difference format according to the present invention, with the steps as follows:

In Step S201, a model of a substance evolution process to be simulated is acquired, wherein the model is a substance-evolution phase field model in a spatial domain, and includes a substance concentration equation and a phase variable equation.

In Step S202, a model equation is transformed to a form that is suitable, when being performed Fourier transform, for solving by using the exponential time-difference format.

In Step S203, the value of $M_i$ at an evolution time, namely the value of Mi at the current iteration from the perspective of computation, is solved based on the phase variable equation and the definition of the substance mobility $M_i$ in the substance evolution model.

In Step S205, after substituting the solved value of $M_i$ thereinto, the substance concentration equation and the phase variable equation perform the Fast Fourier transform.

In Step S207, corresponding iteration steps of the substance concentration equation and the phase variable equation in a frequency domain are solved by using the exponential time-difference format from the fast Fourier transformed result obtained after Step S205.

In Step S209, the solutions to the substance concentration equation and the phase variable equation in the frequency domain are solved by using the iteration steps obtained Step S207.

In Step S213, Inverse Fourier transform is performed on the solutions in the frequency domain as achieved in Step S207 to achieve a solution to the equation of the substance evolution model, namely, the solution of the substance evolution model in the spatial domain.

In Step S215, the solution achieved in Step S213 is saved, wherein the value of substance concentration may describe a process state of a change in the substance evolution.

A judgment is made on whether or not a set substance evolution time is reached, that is, if the number of iteration steps reaches a set value from the perspective of computation. If not, the process returns to Step S103.

If so, the process enters a next step.

In Step S217, a computed solution of the model as obtained from the process above is provided to end the computation. The value of substance concentration therein may describe a result of substance evolution, and is the solving purpose of the model.

FIGS. 3($a$)-3($f$) are diagrams showing the Cu cluster precipitation of initial distribution and after 15,000 steps when an alloy has the composition of Fe—Cu—Mn—Ni.

The gibbs energy in the free energy F is related to the physical components in an alloy system. When a substance has the composition of Fe—Cu—Mn—Ni, F may express the following equation:

$$F=(1.0-(3.0-2.0*\eta)*\eta^2)*((1.4613878411949395*10^{-4}*(-201.3642400*c1*c4-(201.364240*(-2*c4-c3-c2+1.0)-2016,04498)*c4+10672.046*c4+30000.0*c3*c1+36076.894*c1+6842.810456*(\log(c2)-\log(c1))+(6252.0-9865.0*(c2-c3))*c3-39865.0*c2*c3+1740.949*c3-36076.894*c2+2984.135))+(2.0*251.7020800325388218142587919 4465*329*10^{-2}*((c4-c04)*4.75*10^{-4}+(c3-c03)*5.22*10^{-4}+(c2-c02)-3.29*10^{-2}))+((3.0-2.0*\eta)*\eta^2)*(1.4613878411949395*10^{-4}*(c1*(5672.81500*(c4+c3+2*c2-1.0)+42968.802)-c2*(5672.8150*(c4+c3+2*c2-1.0)+42968.802)+(1451.610348*(-2*c4-c3-c2+1.0)-7419.147789)*c1*c4-47841.3*c1*c4+(10672.046-2868.3240*(c2-c4))*c4-(-725.805174*(-2*c4-c3-c2+1.0)^2+7419.147789*(-2*c4-c3-c2+1.0)-9359.746009)*c4+44972.976*c2*c4-26591.0*c3*c1+11345.63*c2*c1-c3*(-259.0*(-c4-2*c3-c2+1.0)-4581.105)+6842.810456*(\log(c2)-\log(c1))+(-1969.5*(c2-c3)^3-8131.0*(c2-c3)+9927.1)*c3+c2*(-5908.5*(c2-c3)^2-8131.0)*c3+26850.0*c2*c3+566.3008361308123))$$

In the equation above, c1, c2, c3 and c4 represent the concentrations of Fe, Cu, Mn and Ni, respectively; and the initial values for simulation may be set by a random distribution, i.e., the atoms are distributed in a system randomly. FIG. 3($a$), FIG. 3($c$) and FIG. 3($e$) are schematic diagrams showing the initial distributions of Cu, Mn and Ni, respectively.

In a simulation process, simulation results of different stages are saved to obtain the evolution from beginning to end, i.e., throughout the change process of cluster precipitation. The iteration is repeated to finally obtain the cluster precipitation and distribution after a set period of time as required. FIG. 3($b$), FIG. 3($d$) and FIG. 3($f$) are schematic diagrams showing the cluster precipitations and distributions of Cu, Mn and Ni, respectively.

As can be seen from the embodiments described above, the method for simulating evolution of a substance by solving based on the exponential time-difference format according to the embodiments of the present application has the following advantages: by establishing the substance evolution model with the phase field model, neither the priori assumption of a structure evolution path of the crystal grains in the substance nor the explicit tracking of the interface location of the crystal grains is needed, which greatly simplifies the complexity in simulation computation; by using the exponential time-difference format, the established phase field model can be solved more rapidly with high accuracy and better stability; and the parallel computation can be performed conveniently by using the exponential time-difference format, which is particularly beneficial to the rapid solving of a large-scale equation set by using a computer.

The embodiments in the present disclosure are described in a progressive manner, a mutual reference can be made to the similar or same parts between the embodiments, and each embodiment focuses on the difference of one embodiment from other embodiments. In particular, system embodiments are essentially similar to method embodiments and thus are described in a simpler way, and a reference may be made to part of the illustration of the method embodiments for points involved.

The specific embodiments of the present disclosure are described above. Other embodiments fall within the scope of the appended claims. In some cases, the operations and steps recorded in the claims can be executed in an order different from that in the embodiments to achieve a desired result as well. In addition, the processes depicted in the accompanying drawings are not necessarily performed based on the illustrated specific order or continuous order to achieve the desired result. In some implementations, multi-task processing and parallel processing are also possible or may be advantageous.

Also, those ordinarily skilled in the art may be further ware of that the units and algorithm steps in each example described in conjunction with the embodiments disclosed herein may be implemented by using electronic hardware, computer software or a combination of these two. For a clear understanding of the interchangeability between the hardware and the software, the composition and steps of each example are described by function in general in the description above. Whether these functions are executed in a form of hardware or software depends on the specific application of the technical solution and design constraints. Those ordinarily skilled in the art may implement the described functions by using different methods for each specific application, but such implementations should not be construed as going beyond the scope of the present application.

The steps of the methods or algorithms described in conjunction with the embodiments disclosed herein may be implemented by using hardware, software modules executed by a process, or a combination of these two. The software modules may be placed in a random-access memory (RAM), an internal memory, a read-only memory (ROM), an electric programmable ROM, an electric erasable programmable ROM, a register, a hard disk, a removable magnetic disk, a CD-ROM, or storage mediums in any other forms as commonly known in the technical field.

The objects, technical solutions and advantageous effects of the present invention are further illustrated in detail with the specific embodiments described above. It should be understood that the description above only involves the specific embodiments of the present invention and is not intended to limit the protection scope of the present invention. Any modifications, equivalent substitutions, improvements and the like made within the spirit and principle of the present invention shall be construed as being included within the protection scope of the present invention.

The invention claimed is:

1. A method of producing desired microstructure of a material with desired physical properties, the method comprising:
   including in the material spatial distribution phases of different crystal structures, crystal grains having different orientations, domains of different structural variants, domains with different electric or magnetic polarizations, and structural defects;
   simulating microstructure evolution of the material, comprising:
      establishing a reaction rate theory model for substance defects, wherein the model is expressed with equations that comprises linear terms having coefficients characterized by matrixes;
      iteratively changing size, shape and spatial arrangement of structural features in the microstructure and solving the equations by using an exponential time-difference format, wherein during the iterative solving, the linear terms with exponential powers of the matrixes as the coefficients are integrated;
      determining gradual evolution of internal concentration of crystal grains relative to internal concentration of adjacent crystal grains over time;
      determining shape change of crystal grains and the movement of an interface location of the concentrations in time; and
      predicting the size distribution of structural features and density of defects of the microstructure and comparing them with an experimental results;
   when the predicted results from the simulation match the experimental results, accepting the size, shape and spatial arrangement of structural features as providing the desired microstructure of the material with desired physical properties.

2. The method according to claim 1, wherein the reaction rate theory model for substance defects comprises: a point defect concentration equation, a double-defect cluster concentration equation, and a defect cluster concentration equation.

3. The method according to claim 1, wherein the equations comprise non-linear terms; and during the iterative solving, the non-linear terms are numerically solved.

4. The method according to claim 3, wherein during the iterative solving, the non-linear terms are processed by using a predictor-corrector method.

5. A computing device, characterized by comprising:
   at least one memory for storing at least one program; and
   at least one processor for executing the at least one program stored in the memory, wherein when the at least one program stored in the memory is executed, the processor is configured to execute the method of producing desired microstructure of a material with desired physical properties according to claim 1.

6. A method of producing desired microstructure of a substance with desired physical Properties, the method comprising:
   including in the substance spatial distribution phases of different crystal structures, crystal grains having different orientations, domains of different structural variants, domains with different electric or magnetic polarizations, and structural defects;
   simulating evolution of the substance, comprising:
      modeling an evolution process of the substance by using a phase field model to obtain an equation set of an evolution model of the substance, wherein the phase field model comprises high-order spatial derivatives, and the equation set of the evolution model of the substance comprises a substance concentration equation and a phase variable equation;
      iteratively changing size, shape and spatial arrangement of structural features in the microstructure and solving the equation set of the evolution model, wherein during the iterative solving, the equation set of the evolution model of the substance is transformed; forms of the substance concentration equation and the phase variable equation in a frequency domain are obtained by using a fast Fourier algorithm, including forms of the high-order spatial derivatives in the frequency domain as coefficients of linear terms; the forms of the substance concentration equation and the phase variable equation in the frequency domain are solved by using an exponential time-difference format, and during the solving, the high-order spatial derivatives are solved by using the exponential time-difference format to integrate the linear terms, which take exponential powers of the forms of the high-order spatial derivatives in the frequency domain as the coefficients; and a solved result is subjected to inverse Fourier transform;
      determining gradual evolution of internal concentration of crystal grains relative to internal concentration of adjacent crystal grains over time;
      determining shape change of crystal grains and the movement of an interface location of the concentrations in time; and
      predicting the size distribution of structural features and density of defects of the microstructure and comparing them with an experimental results;
   when the predicted results from the simulation match the experimental results, accepting the size, shape and spatial arrangement of structural features as providing the desired microstructure of the substance with desired physical properties.

7. The method according to claim 6, wherein the phase field model comprises non-linear terms; and during the solving, the non-linear terms are numerically solved.

8. The method according to claim 7, wherein during the solving, the non-linear terms are split and controlled by a linear operator.

9. The method according to claim 7, wherein when the forms of the substance concentration equation and the phase variable equation in the frequency domain are solved by using the exponential time-difference format, multi-step approximation, a Runge-Kutta method or prediction-correction is performed on the non-linear terms to implement the numeric solving.

10. A computing device, characterized by comprising:
    at least one memory for storing at least one program; and
    at least one processor for executing the at least one program stored in the memory, wherein when the at least one program stored in the memory is executed, the processor is configured to execute the method of producing desired microstructure of a substance with desired physical properties according to claim 6.

\* \* \* \* \*